US006778273B2

(12) United States Patent
Norton et al.

(10) Patent No.: US 6,778,273 B2
(45) Date of Patent: Aug. 17, 2004

(54) POLARIMETRIC SCATTEROMETER FOR CRITICAL DIMENSION MEASUREMENTS OF PERIODIC STRUCTURES

(75) Inventors: Adam E. Norton, Palo Alto, CA (US); Abdurrahman Sezginer, Los Gatos, CA (US); Fred E. Stanke, Cupertino, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/112,138

(22) Filed: Mar. 29, 2002

(65) Prior Publication Data

US 2003/0020912 A1 Jan. 30, 2003

Related U.S. Application Data

(60) Provisional application No. 60/280,714, filed on Mar. 30, 2001.

(51) Int. Cl.[7] .................................................. G01J 4/00
(52) U.S. Cl. ........................................ 356/364; 356/445
(58) Field of Search ................................ 356/364, 369, 356/237.1, 237.2, 237.3, 237.4, 237.5, 445, 448

(56) References Cited

U.S. PATENT DOCUMENTS

| | | | | | |
|---|---|---|---|---|---|
| 3,858,983 | A | * | 1/1975 | Foster et al. ................. | 356/448 |
| 4,745,526 | A | | 5/1988 | Sestak .......................... | 362/35 |
| 4,933,567 | A | * | 6/1990 | Silva et al. ................... | 356/369 |
| 5,042,951 | A | * | 8/1991 | Gold et al. ................... | 356/369 |
| 5,394,247 | A | * | 2/1995 | Vahey et al. ................. | 356/429 |
| 5,432,607 | A | | 7/1995 | Taubenblatt ................. | 356/364 |
| 5,640,244 | A | * | 6/1997 | Hellstrom et al. ........... | 356/446 |
| 5,726,756 | A | * | 3/1998 | Aki et al. ................. | 356/237.2 |
| 5,801,824 | A | * | 9/1998 | Henley ..................... | 356/237.2 |
| 5,910,842 | A | * | 6/1999 | Piwonka-Corle et al. ... | 356/369 |
| 5,995,218 | A | | 11/1999 | Ide ........................... | 356/237.1 |
| 6,038,026 | A | * | 3/2000 | Maris .......................... | 356/514 |
| 6,297,880 | B1 | * | 10/2001 | Rosencwaig et al. ....... | 356/369 |
| 6,362,881 | B1 | * | 3/2002 | Pickering et al. ........... | 356/369 |
| 6,423,977 | B1 | * | 7/2002 | Hayasaki et al. ........ | 356/237.5 |
| 6,473,186 | B2 | * | 10/2002 | Kawasaki et al. .......... | 356/512 |
| 6,493,064 | B2 | * | 12/2002 | Cabiri et al. ................ | 356/400 |
| 6,507,394 | B1 | * | 1/2003 | Cheng et al. ............ | 356/237.5 |
| 2002/0018217 | A1 | * | 2/2002 | Weber-Grabau et al. .... | 356/601 |

FOREIGN PATENT DOCUMENTS

| | | | |
|---|---|---|---|
| JP | 58034310 | 2/1983 | ........... G01B/11/30 |
| JP | 05060527 | 3/1993 | ........... G01B/11/24 |
| JP | 08190066 | 7/1996 | ........... G02B/26/10 |
| JP | 09138364 | 5/1997 | ........... G02B/26/10 |
| JP | 10300861 | 11/1998 | ........... G01W/1/14 |
| JP | 11295785 | 10/1999 | ........... G03B/15/02 |
| JP | 2001/305071 | 10/2001 | ......... G01N/21/956 |

OTHER PUBLICATIONS

"Automated Multiple Angle of Incidence Ellipsometer System," *IBM Technical Disclosure Bulletin*, vol. 32, No. 9A, Feb. 1990, pp. 417–424.

"Automated, Remote, Programmable, Ellipometer Drive Mechanism," *IBM Techniocal Disclosure Bulletin*, vol. 31, No. 9, Feb. 1989, pp. 108–113.

* cited by examiner

Primary Examiner—Michael Stafira
Assistant Examiner—Juan D Valentin, II
(74) Attorney, Agent, or Firm—Stallman & Pollock LLP

(57) ABSTRACT

An optical measurement system for evaluating a sample has a azimuthally rotatable measurement head. A motor-driven rotating mechanism is coupled to the measurement head to allow the optics to rotate with respect to the sample. In particular, a preferred embodiment is a polarimetric scatterometer (FIG. 1) for measuring optical properties of a periodic structure on a wafer sample (12). This scatterometer has optics (30) directing a polarized illumination beam at nonnormal incidence onto the periodic structure. In addition to a polarizer (8), the illumination path can also be provided with an E-O modulator for modulating the polarization. The measurement head optics also collect light reflected from the periodic structure and feed that light to a spectrometer (17) for measurement. A polarization beamsplitter (18) is provided in the collection path so that both S and P polarization from the sample can be separately measured. The entire measurement head can be mounted for rotation of the plane of incidence to different azimuthal directions relative to the periodic structures on the wafer. The instrument can be integrated within a wafer process tool in which wafers may be provided at arbitrary orientation.

12 Claims, 1 Drawing Sheet

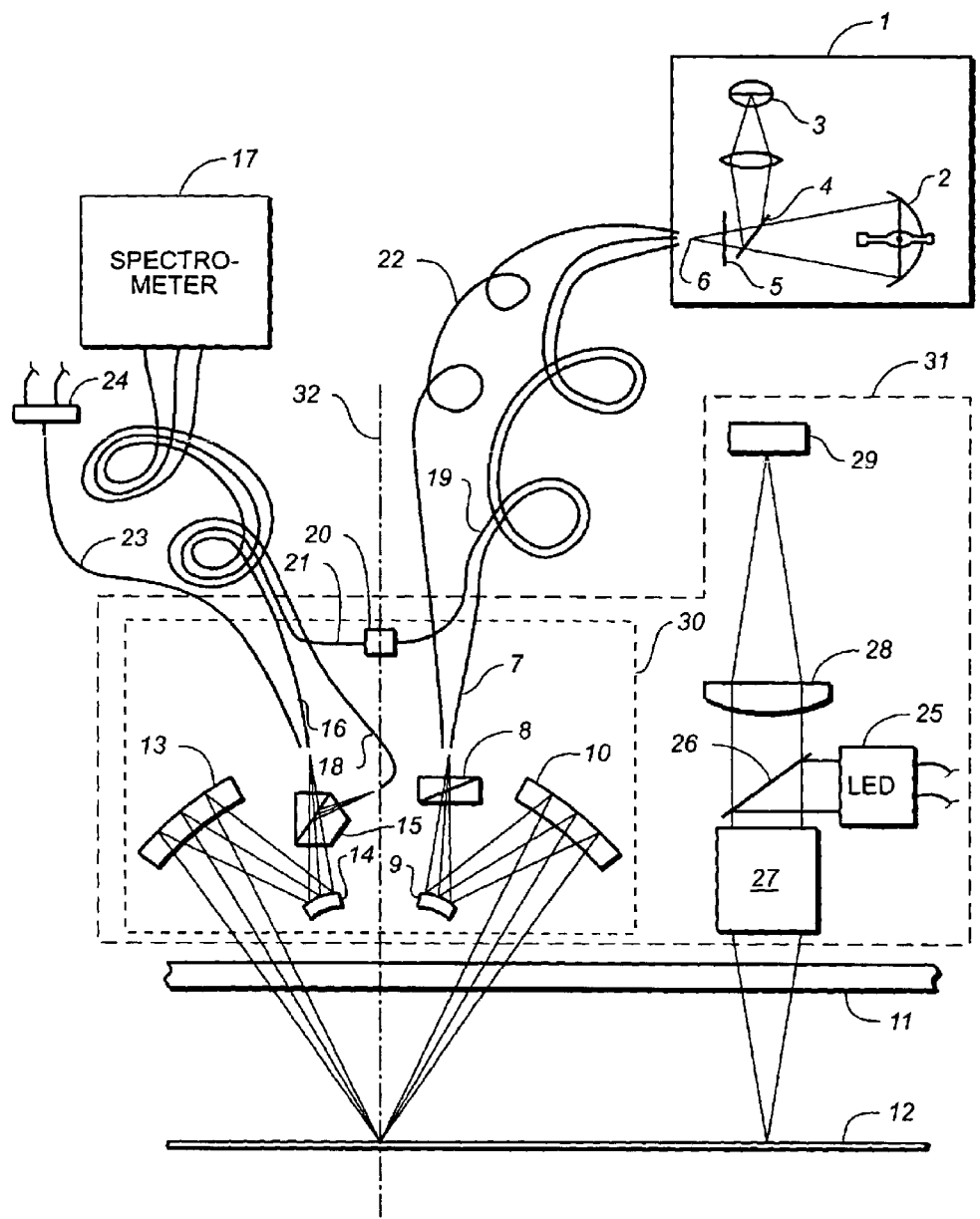
FIG._1

POLARIMETRIC SCATTEROMETER FOR CRITICAL DIMENSION MEASUREMENTS OF PERIODIC STRUCTURES

CROSS-REFERENCE TO RELATED APPLICATION

This application claims priority under 35 U.S.C. §119(e) from prior U.S. provisional application No. 60/280,714, filed Mar. 30, 2001.

TECHNICAL FIELD

The present invention relates to optical measurement instruments, such as scatterometers, reflectometers and ellipsometers, for wafer testing during the manufacture of integrated circuits.

BACKGROUND ART

In the manufacture of integrated circuits, very thin lines or holes down to 100 nm or sometimes smaller are patterned into photo resist and then often transferred using an etching process into a layer of material below on a silicon wafer. It is extremely important to inspect and control the width and profile (also known as critical dimensions or CDs) of these lines or holes. Traditionally the inspection of CDs that are smaller than the wavelength of visible light has been done using large and expensive scanning electron microscopes. In many cases, however, manufacturers would like to have measurements immediately after the photoresist has been patterned or etched to have tight control of the process before it drifts out of spec. Testing the wafer early during production and controlling the fabrication steps according to the test results helps to keep production costs low and to keep yields high. Ideally the measurement tool would be integrated into the wafer track that develops the photoresist or integrated into the wafer etching tool.

In typical stand-alone instruments, the wafer is moved on a stage, while the measurement optics remain stationary. Also, when the angle of incidence on the wafer is other than zero (e.g. in ellipsometers), the wafer is preferably oriented so that the plane of incidence is perpendicular to the lines on the wafer.

An integrated CD measurement tool must be both fast and compact, and must not damage the wafer under test. The size constraints usually mean that the wafer can not be translated across its full diameter in 2 horizontal axes to measure different sites on the wafer. Hence, a portion of the test instrument must move in one or more axes to cover the wafer. The wafer might also rotate, but this is less desirable in systems without full X-Y movement that have a preferred measurement orientation with respect to certain wafer features. Furthermore, some wafer processing tools into which the present invention may be integrated require that the wafer not move so that the processing tool robot can pick up the wafer at any time. The wafer may also be loaded into the measurement tool at an arbitrary angle creating further complications for instruments that have a preferred measurement orientation with respect to certain wafer features.

One general technique that has promise for integrated CD measurements is scatterometry. This technique takes advantage of the fact that an array of small lines or holes affect the properties of the light in the zero order that is reflected (or, for transparent samples, transmitted) from such an array. Various measurable properties of the zero-order light will vary depending on the dimensions of the structure on the wafer. Often such parameters are measured versus wavelength, and in some cases, versus angle of incidence on the sample. Normal-incidence spectroscopic reflectometers show particular promise because they can be used with the wafers in any arbitrary orientation.

Typically, CD measurements have been made using instruments such as ellipsometers or reflectometers that were originally designed to measure film thickness. The data from such instruments is usually fed to a processor, which analyzes the measurements, usually by accessing a library of theoretically generated data for a range of array dimensions and film properties near those of the expected dimensions of the sample. The measured data are compared to the library and a best fit match to a data set in the library is found. The processor then outputs the corresponding dimensions.

Since there are multiple independent unknown variables that may need to be measured, such as line width, line edge slope, top film thickness, underlying film thickness, or film refractive index, it is desirable that the measurement technique measure as many multiple independent parameters as is practical.

Coulombe et al. ('Ellipsometric-Scatterometry for sub-0.1 $\mu$m CD measurements, 'SPIE, Vol. 3332, p. 282–293) investigated reflectometry and ellipsometry of line gratings as a function of angle of incidence and azimuth.

One object of the present invention was to create a scatterometer for measuring CDs and possibly overlay error on periodic structures that is compact and well suited for integration into a wafer process tool.

Another object was to be able to measure on structures at different azimuth orientations.

Another object was to be able to collect as much independent data as practical from the sample. Another object was to be able to measure structures 100 nm wide or smaller.

Another object of the invention was to be able to measure structures at the optimal azimuth angle or angles regardless of the azimuth orientation of the sample.

SUMMARY OF THE INVENTION

These objects are met by a polarimetric scatterometry instrument that optically measures properties of periodic structures on a sample, using polarized light incident upon such structures. The polarized light is incident on samples at non-normal incidence (defined here as greater than 4° from perpendicular to the sample surface), and the reflected light is collected, fed into a spectrometer, and the measurements used to determine the width, profile or thickness of features associated with the illuminated periodic structures, or used to determine relative registration error between overlapping periodic structures.

The instrument includes one or more broad-spectrum light sources, e.g. a xenon lamp and a deuterium lamp, and the light from such sources may be supplied to a movable measurement head via one or more optical fibers. Likewise, light collected by the measurement head optics may be delivered to the spectrometer via one or more optical fibers. At least one polarizing element (fixed or rotatable) is situated in the beam path, with preferably a polarizer in each of the illumination and collection paths, and there may also be a polarization modulating element associated with any of the polarizers.

The measurement head may be rotated by a motor-driven mechanism to orient the plane of incidence (and collection) to different azimuth orientations $\theta$ relative to the sample. This concept of a measurement head that can be rotated as a unit to different azimuth directions can be extended to other related instruments that have a non-normal incident beam or other directional anisotropies in their optics, including for example spectroscopic ellipsometers. In addition to employing non-normal incidence and collection, ellipsometers also include rotating compensators and analyzers which, like the polarimetric scatterometer, establish a specific polarization direction to the light. The ability to rotate the measurement head allows measurements to be made on wafers at any arbitrary orientation.

The instrument, or at least the measurement head thereof, can be integrated into a wafer processing tool and wafer samples delivered to the instrument for measurement. The measurement head then moves laterally over the wafer (or the wafer moves on a stage) to specific measurement spots. Spectral reflectance measurement at each spot is then made with the polarized light at preferably three or more different azimuth angles by rotating the head. In some cases, it may be preferable for the sake of simplicity to measure the spectral reflectance at one azimuth angle, where the head is rotated so the plane of incidence on the wafer is, e.g., perpendicular to the array of periodic structures on the grating.

BRIEF DESCRIPTION OF THE DRAWINGS

FIG. 1 is a schematic side plan view of a preferred embodiment of a polarimetric scatterometer of the present invention.

BEST MODE OF CARRYING OUT THE INVENTION

With reference to FIG. 1, the light box 1 has a high pressure xenon lamp 2 to provide illumination between 220 and 1100 nm. It also has a deuterium lamp 3 to provide deep-UV light between 190 and 240 nm. The shorter wavelength UV light helps give better results on smaller structures. A mirror 4 can be moved into the beam path to select between the two light sources. A shutter 5 can flip into the beam to cut off all light. The shutter both protects the optics from excessive UV light and allows measurement of the detectors' background signal. The light box optics create an image 6 of the sources that is large enough to illuminate several multi-mode optical fibers 7, 19 and 22. One of these fibers 7 preferably has a core diameter of 100 microns. The output end of fiber 7 is imaged onto the wafer 12 with a demagnification of approximately 2× using curved mirrors 9 and 10. The angle of incidence on the wafer is non-normal, i.e. greater than 4° away from perpendicular to the wafer surface, and is typically anywhere between 5° and 50°. A fused silica window 11 protects the wafer 12 from particles generated from the moving optics, and also protects the optics from outgassing from the wafer.

A polarizer 8 linearly polarizes the light that is incident onto the wafer. This polarization is selected to maximize the sensitivity of the optical measurement to the parameters of the sample. In a preferred implementation, polarizer 8 allows only the S-polarized light onto the sample. In a more complex version of the invention, the polarizer 8 could be made to rotate to collect even more information about the sample. Also a rotating waveplate or electro-optic modulator (Pockels or Kerr effect based) could be placed after polarizer 8 also to collect more information on the sample's properties.

Mirrors 9 and 10 have their centers of curvature lying on or near a line between the output end of fiber 7 and its image on the wafer. These mirrors fold the light path so that the non-normal incidence does not lead to unnecessarily large footprint for the measurement head. This is desired so that the head can be integrated within a wafer process tool. Mirror 9 is a first surface convex mirror, while 10 is a concave fused silica mangin mirror. The two mirrors 9 and 10 correct the chromatic and other aberrations introduced by the window 11 and the polarizer 8 so that the image of the fiber end has near diffraction-limited quality from 190 to 1100 nm. A prescription for a representation optical design is given in a appendix A. This prescription is optimized for a particular angle of incidence, window thickness, working distance, etc. Modifications for other particular design configurations could be made by one skilled in the art.

The light reflected from the wafer is collected and imaged by mirrors 13 and 14 that are similar to mirrors 10 and 9, with their centers of curvature preferably on a line between the measurement spot on the wafer sample 12 and the input to the optical fiber 16, and correcting for any aberrations introduced by window 11 and polarizer 15. The light travels through a beamsplitting crystal polarizer 15 preferably made from alpha barium borate. The beamsplitting polarizer 15 directs images of the wafer onto the input ends of fibers 16 and 18. Fiber 16 receives S-polarized light while fiber 18 receives P-polarized light. The two fibers 16 and 18 have smaller core diameters than fiber 7 so that the measurements are not overly sensitive to focus. The diameter of the end of fibers 18 and 16 determine the geometric size of the measurement spot on the wafer, typically less than 200 $\mu$m diameter. A less complex version of this apparatus would have the beamsplitting polarizer 15 replaced by a simple polarizer so that only one polarization is detected. Another version would have polarizer 15 omitted, but that version would be less useful in measuring three-dimensional grating structures such as arrays of holes. More complex versions would replace 15 with a rotating polarizer, or fixed polarizer with rotating waveplate or electro-optic modulator.

Fibers 16 and 18 carry the two polarizations of reflected light to a multi-channel spectrometer 17 that has the capability of measuring the spectrum from each fiber simultaneously. Spectrometer 17 would have either multiple linear detector arrays or a two dimensional detector array. Multiple standard spectrometers could also be used in place of the multi-channel spectrometer 17. Alternatively, the illumination or detection could use a monochromator to serially perform measurements at various wavelengths of light.

Another fiber 19 exits the light box and closely follows the path of fiber 7 until it enters the measurement head 30. At that point it is coupled to another fiber 21 with a connector 20. Fiber 21 also closely parallels fibers 16 and 18. Fiber 21 also enters spectrometer 17, where its spectrum is used to correct for variations in the lamp intensity or transmission of the fibers versus measurement head position.

Alternatively, fiber 21 could direct its light to a photodiode (not shown) if the intensity variations are not substantially spectrally dependent. Ideally the fibers are routed so that as the measurement head 30 moves, the radius of any bends in the fiber remain constant.

The data from the spectrometer or photodiode preferably goes to a processor (not shown) where it is converted into determinations of the parameters of the structure on the wafer at the measurement spot. For example, the parameters might be the thicknesses of films, line width (critical dimension or CD), the sidewall slope of lines, etc. In one embodiment, the data is converted into spectral, absolute, polarized reflectance and compared to the spectrum library to find the best match and therefore the unknown structure parameters. There are many alternative approaches to process the data from the spectrometers to yield structure parameters. For example, the theoretical responses for comparison to the processed spectrometer data may be calculated with model parameters determined after the data is obtained. This is in distinction to comparing to library responses which are precomputed for predetermined parameter values and stored. In yet another embodiment, parameters of structure may be calculated directly from the spectrometer data, i.e., without comparing to model results as an intermediate step.

A third fiber 22 exits the lamp house 1 and has its output end in the object plane next to the end of fiber 7. The light from fiber 22 travels through the optical system (elements 8–10 and 13–15), reflecting off the wafer and forming an image of the exit end of fiber 22 onto the entrance end of fiber 23. Fibers 22 and 23 are the same size so that the signal which is detected by a photodiode 24 is extremely sensitive to wafer focus. Autofocus is performed by scanning the measurement head 30 in Z and moving to the Z position that maximizes signal on photodiode 24. The light source for fiber 22 could also be a laser.

While the scatterometer system described above uses a remote light source and remote spectrometer (i.e., not mounted to the movable measurement head), and couples these elements to the measurement head optics via a set of optical fibers, it is also possible to mount one or both of these elements directly to the measurement head. The additional mass of such a measurement head may slow the movement of the head somewhat, but the head will still be usable, especially if the source and spectrometer are reasonably lightweight and if the motors used to move the head assembly are reasonably powerful. An advantage of direct mounting is that twisting of the optical fibers during azimuthal rotation of the measurement head can be avoided. Instead, the light from the source is directed to the sample and reflected light is collected from the sample in the normal manner, i.e. with mirrors and lenses.

The measurement head 30 is mounted to a rotating mechanism (not shown) that allows it to rotate in azimuth around the vertical axis 32. In an integrated wafer processing station, the head 30 might also be mounted to an X-Y mechanism (not shown) for providing lateral motion of the head so that it can measure different points on the wafer without having to move the wafer. Alternatively, an X-Y stage could be provided to move the wafer, especially for stand-alone measurement systems. In that case, X-Y lateral motion of the optical measurement head is unnecessary. If desired, a reduced motion stage, such as ½X,½Y stage, with or without wafer stage θ rotation, or a polar coordinate (R, θ) stage, can be used to reduce the footprint required by the wafer. Yet another configuration would have the wafer placed on a rotary stage, and the rotatable measurement head 30 mounted for radial motion. Basic construction details of rotation and X-Y drive mechanisms are well known in the art and are applicable here. The rotational axis of the measurement head 30 should coincide with the symmetry axis 32 of the measurement optics and intersect the illuminating beam at the spot on the wafer sample 12. Alternatively, a controller may have information about the relative positions of the two axes, and position the measurement head with respect to the wafer accordingly. A complete 360° rotating range is preferred, although a 180° range would also be acceptable in many cases. A driver motor can be used, coupled to a rotatable plate on which the measurement head optics assembly is mounted. If needed, this entire unit (motor, plate, and optics) can then be mounted to the X-Y mechanism, along with the other elements within dashed box 31.

Collecting data at multiple azimuth angles on a grating structure on the wafer produces additional independent measurements that reveal more information about the structure and allows either measurement of more unknown parameters of the structure or more robust determination of a few unknowns. In the case where the wafer can not be rotated arbitrarily, the measurement head azimuth rotation also allows the plane of incidence to be aligned in the preferred perpendicular direction relative to the grating lines even when multiple azimuth angles are not needed. Furthermore, the ability to measure at two azimuth angles 180° apart can be used to reduce the sensitivity of the measurements to wafer tilt and other asymmetries in the optical system. As previously noted, this concept can be extended to related optical instruments, such as spectroscopic ellipsometers, that also have directional anisotropies in their optics. Like the preferred polarimetric scatterometer shown in the FIGURE, ellipsometers also have non-normal incidence and collection of a light beam. They also have specific polarization directions established by rotatable compensators and analyzers. Being able to rotate an optical measurement head in a range of azimuthal directions allows the instrument to be used with wafers or other samples at arbitrary orientations, since the head can be rotated to the desired measurement orientation.

Everything within outline 31 is mounted to the X-Y stage. The elements outside 31 may optionally be located remotely where they do not occupy the limited space available inside a wafer process tool. Within 31 there is also a viewing subsystem (elements 25–29) to view the wafer patterns and allow the exact position and orientation of the wafer to be determined relative to the X-Y stage or measurement head. A large LED 25 provides the illumination. Preferably 25 is a two color LED so that the second color can be used in case the first does not provide sufficient contrast. Alternatively, two LEDs of different colors with a dichroic beamsplitter to combine both beams could replace the single LED 25. A conventional visible beamsplitter 26 directs the illumination to an objective 27. The LED 25 is preferably placed near the entrance (or upper) pupil of 27. There are many alternative sources of illumination for a viewing system. Objective 27 and tube lens 28 form an image of the wafer on a CCD video camera 29. The position of the center of the field of view of camera 29 on the wafer is measured and calibrated (it has a known fixed offset distance) relative to the position of the image of fiber 7 on the wafer. The image from the camera 29 is fed into a pattern recognition subsystem that determines the position and angle of the wafer pattern.

A second angle of incidence can be accommodated inside measurement head 30 by having a second set of optics (not shown) with a different angle of incidence oriented in a plane separate from that of the first angle of incidence. This second angle of incidence can likewise be changed to other azimuth directions relative to the sample 12 by rotating the measurement head 30.

-13-

Appendix A

GENERAL LENS DATA:

```
Surfaces                : 22
Stop                    : 2
System Aperture         :Object Space NA = 0.07
Glass Catalogs          :schott MISC
Ray Aiming              :Paraxial Reference, Cache On
    X Pupil shift       : 0
    Y Pupil shift       : 0
    Z Pupil shift       : 0
Apodization             :Uniform, factor = 1.00000E+000
Effective Focal Length  : 9.003085 (in air)
Effective Focal Length  : 9.003085 (in image space)
Back Focal Length       : -20.82646
Total Track             : 1000
Image Space F/#         : 0.06415
Paraxial Working F/#    : 19.95104
Working F/#             : 21.56443
Image Space NA          : 0.02505348
Object Space NA         : 0.07
Stop Radius             : 70.17213
Paraxial Image Height   : 0.03360017
Paraxial Magnification  : -2.800015
Entrance Pupil Diameter : 140.3443
Entrance Pupil Position : 1000
Exit Pupil Diameter     : 1.267607
Exit Pupil Position     : -23.90778
Field Type              :Object height in Millimeters
Maximum Field           : 0.012
Primary Wave            : 0.55
Lens Units              :Millimeters
Angular Magnification   : 110.7159
```

-14-

Fields : 3
Field Type: Object height in Millimeters

| # | X-Value | Y-Value | Weight |
|---|---------|---------|----------|
| 1 | 0.000000 | 0.000000 | 1.000000 |
| 2 | 0.000000 | 0.012000 | 1.000000 |
| 3 | 0.000000 | -0.012000 | 1.000000 |

Vignetting Factors:

| # | VDX | VDY | VCX | VCY | VAN |
|---|-----|-----|-----|-----|-----|
| 1 | 0.000000 | 0.000000 | 0.000000 | 0.000000 | 0.000000 |
| 2 | 0.000000 | 0.000000 | 0.000000 | 0.000000 | 0.000000 |
| 3 | 0.000000 | 0.000000 | 0.000000 | 0.000000 | 0.000000 |

Wavelengths : 7
Units: Microns

| # | Value | Weight |
|---|-------|--------|
| 1 | 0.550000 | 1.000000 |
| 2 | 0.190000 | 1.000000 |
| 3 | 0.800000 | 1.000000 |
| 4 | 0.300000 | 1.000000 |
| 5 | 0.400000 | 1.000000 |
| 6 | 0.600000 | 1.000000 |
| 7 | 0.700000 | 1.000000 |

| Surf | Type | Comment | Radius | Thickness | Glass | Diameter | Conic |
|---|---|---|---|---|---|---|---|
| OBJ | STANDARD | | Infinity | 0 | | 0.024 | 0 |
| 1 | COORDBRK | AOI | - | 1000 | | - | - |
| STO | STANDARD | STOP | Infinity | -1000 | | 140.3443 | 0 |
| 3 | COORDBRK | | - | 0 | | - | - |
| 4 | STANDARD | WAFER AGAIN | Infinity | 15 | | 0.024 | 0 |
| 5 | STANDARD | WINDOW | Infinity | 3 | SILICA | 34.55152 | 0 |
| 6 | STANDARD | | Infinity | 39.64854 | | 38.19851 | 0 |
| 7 | COORDBRK | BACK TO OBJECT | - | -57.64854 | | - | - |
| 8 | COORDBRK | OPTIC AXIS TILT | - | 57.64854 | | - | - |
| 9 | COORDBRK | MANGIN TILT | - | 0 | | - | - |
| 10 | STANDARD | | -44.43256 | 0 | SILICA | 63.98901 | 0 |
| 11 | COORDBRK | MANGIN UNTILT | - | 2 | | - | - |
| 12 | STANDARD | | -45.89193 | -2 | MIRROR | 66.33014 | 0 |
| 13 | COORDBRK | MANGIN TILT 2 | - | 0 | | - | - |
| 14 | STANDARD | | -44.43256 | 0 | | 63.4319 | 0 |
| 15 | COORDBRK | MANGIN UNTILT 2 | - | -30.53794 | | - | - |
| 16 | STANDARD | | -12.52719 | 15.1287 | MIRROR | 9.513147 | 0 |
| 17 | COORDBRK | | - | 0 | | - | - |
| 18 | STANDARD | POLARIZER | Infinity | 3 | QUARTZ | 4 | 0 |
| 19 | STANDARD | | Infinity | 0 | | 4 | 0 |
| 20 | COORDBRK | | - | 3 | | - | - |
| 21 | COORDBRK | FIBER TILT | - | 0 | | - | - |
| IMA | STANDARD | | Infinity | | | 1.809468 | 0 |

SURFACE DATA DETAIL:

Surface OBJ      : STANDARD
Surface   1      : COORDBRK
  Comment        : AOI
  Decenter X     : 0
  Decenter Y     : 0
  Tilt About X   : 45
  Tilt About Y   : 0
  Tilt About Z   : 0
  Order          : Decenter then tilt
Surface STO      : STANDARD
  Comment        : STOP
Surface   3      : COORDBRK
  Decenter X     : 0

-16-

```
            Decenter Y      :  0
            Tilt About X    : -45
            Tilt About Y    :  0
            Tilt About Z    :  0
         5  Order           : Decenter then tilt
            Surface   4     : STANDARD
            Comment         : WAFER AGAIN
            Surface   5     : STANDARD
            Comment         : WINDOW
        10  Coating         : AR
            Surface   6     : STANDARD
            Coating         : AR
            Surface   7     : COORDBRK
            Comment         : BACK TO OBJECT
        15  Decenter X      :  0
            Decenter Y      :  0
            Tilt About X    :  0
            Tilt About Y    :  0
            Tilt About Z    :  0
        20  Order           : Decenter then tilt
            Surface   8     : COORDBRK
            Comment         : OPTIC AXIS TILT
            Decenter X      :  0
            Decenter Y      :  0
        25  Tilt About X    :  11.91948
            Tilt About Y    :  0
            Tilt About Z    :  0
            Order           : Decenter then tilt
            Surface   9     : COORDBRK
        30  Comment         : MANGIN TILT
            Decenter X      :  0
            Decenter Y      :  0
            Tilt About X    : -0.099107841
            Tilt About Y    :  0
        35  Tilt About Z    :  0
            Order           : Decenter then tilt
```

-17-

```
           Surface  10      : STANDARD
           Coating          : AR
           Surface  11      : COORDBRK
           Comment          : MANGIN UNTILT
     5     Decenter X       :  0
           Decenter Y       :  0
           Tilt About X     :  0.099107841
           Tilt About Y     :  0
           Tilt About Z     :  0
    10     Order            : Decenter then tilt
           Surface  12      : STANDARD
           Surface  13      : COORDBRK
           Comment          : MANGIN TILT 2
           Decenter X       :  0
    15     Decenter Y       :  0
           Tilt About X     : -0.099107841
           Tilt About Y     :  0
           Tilt About Z     :  0
           Order            : Decenter then tilt
    20     Surface  14      : STANDARD
           Coating          : AR
           Surface  15      : COORDBRK
           Comment          : MANGIN UNTILT 2
           Decenter X       :  0
    25     Decenter Y       :  0
           Tilt About X     :  0.099107841
           Tilt About Y     :  0
           Tilt About Z     :  0
           Order            : Decenter then tilt
    30     Surface  16      : STANDARD
           Surface  17      : COORDBRK
           Decenter X       :  0
           Decenter Y       :  0
           Tilt About X     : -10
    35     Tilt About Y     :  0
           Tilt About Z     :  0
```

-18-

```
        Order            : Decenter then tilt
        Surface  18      : STANDARD
         Comment         : POLARIZER
         Aperture        : Floating Aperture
         Maximum Radius:             2
        Surface  19      : STANDARD
         Aperture        : Floating Aperture
         Maximum Radius:             2
        Surface  20      : COORDBRK
         Decenter X      :   0
         Decenter Y      :   0
         Tilt About X    :  10
         Tilt About Y    :   0
         Tilt About Z    :   0
         Order           : Decenter then tilt
        Surface  21      : COORDBRK
         Comment         : FIBER TILT
         Decenter X      :   0
         Decenter Y      :   0
         Tilt About X    :   0
         Tilt About Y    :   0
         Tilt About Z    :   0
         Order           : Decenter then tilt
        Surface IMA      : STANDARD
```

COATING DEFINITIONS:

| Material | Thickness | Absolute | Loop |
|---|---|---|---|
| Coating AR, 1 layer(s) | | | |
| MGF2 | 0.250000 | 0 | 0 |

What is claimed is:

1. An apparatus for measuring the optical properties of a periodic structure on a sample, comprising:

a movable measurement head having optics directing a polarized illumination beam onto the periodic structure on the sample and collecting light reflected from a measurement spot of the periodic structure, wherein the movable measurement head is rotatable in azimuth relative to the sample, wherein the measurement spot defined by the measurement head has a size less than 200 microns, and wherein the illumination beam directed by the measurement head optics is incident on the sample at an angle greater than 4 degrees; and a near point-like light source, a tilted convex mirror, a tilted concave mangin mirror, said mirrors forming a well-corrected image with light focused through a window tilted with respect to a chief ray, said mirrors having their centers of curvature located on a line between the source and image.

2. The apparatus of claim 1 where the image is corrected for wavelengths greater than 400 nm.

3. The apparatus of claim 1 where a polarizer lies between the source and the convex mirror.

4. An apparatus for measuring the optical properties of a periodic structure on a sample, comprising:

a movable measurement head having optics directing a polarized illumination beam onto the periodic structure on the sample and collecting light reflected from a measurement spot of the periodic structure, wherein the movable measurement head is rotatable in azimuth relative to the sample and wherein the measurement spot defined by the measurement head has a size less than 200 microns; and further including a separate fiber to monitor transmission changes in said polarized illumination beam.

5. An apparatus for measuring the optical properties of a periodic structure on a sample, comprising:

a movable measurement head having optics directing an illumination beam at an incidence angle greater than 4° onto the periodic structure on the sample and collecting light reflected from a measurement spot of the periodic structure, wherein the movable measurement head is rotatable in azimuth relative to the sample wherein the measurement spot defined by the measurement head has a size less than 200 microns; and a near point-like light source, a tilted convex mirror, a tilted concave mangin mirror, said mirrors forming a well-corrected image with light focused through a window tilted with respect to a chief ray, said mirrors having their centers of curvature located on a line between the source and image.

6. The apparatus of claim 5 where the image is corrected for wavelengths greater than 400 nm.

7. An apparatus for measuring the optical properties of a periodic structure on a sample, comprising:

a movable measurement head having optics directing an illumination beam at an incidence angle greater than 4° onto the periodic structure on the sample and collecting light reflected from a measurement spot of the periodic structure, wherein the movable measurement head is rotatable in azimuth relative to the sample wherein the measurement spot defined by the measurement head has a size less than 200 microns; and further including a separate fiber to monitor transmission changes in said polarized illumination beam.

8. An apparatus for evaluating a periodic structure on a semiconductor wafer, comprising:

a broadband light source for generating a probe beam;

an optical assembly for coupling the probe beam from the broadband light source to a spot on the surface of the semiconductor wafer including the periodic structure, the optical assembly further collecting light specularly reflected from the sample;

a spectrometer operable to measure the collected specularly reflected light and generate an output signal as a function of wavelength; and a rotating mechanism coupled to the optical assembly for rotating the optical assembly such that a plane defining the incident and specularly reflected light is rotated thereby varying the direction in which the probe beam impinges upon the sample wherein the rotational axis of the optical assembly intersects with the probe beam spot on the sample.

9. An apparatus according to claim 8, wherein:

the optical assembly is coupled to at least one of the broadband light source and the spectrometer by at least one optical fiber capable of carrying the probe beam.

10. An apparatus according to claim 8, wherein:

the spectrometer is rigidly attached to the optical assembly.

11. An apparatus according to claim 8, wherein:

the broadband light source is rigidly attached to the optical assembly.

12. An apparatus according to claim 8, wherein:

the spectrometer is further operable to measure characteristics of the periodic structure selected from the group consisting of width, profile, and thickness.

* * * * *